United States Patent [19]
Okuda et al.

[11] Patent Number: 5,837,050
[45] Date of Patent: Nov. 17, 1998

[54] ULTRAFINE IRON-CONTAINING RUTILE TITANIUM OXIDE AND PROCESS FOR PRODUCING THE SAME

[75] Inventors: Haruo Okuda; Hideo Futamata; Akihito Sakai; Masakazu Hattori, all of Yokkaichi, Japan

[73] Assignee: Ishihara Sangyo Kaisha, Ltd., Osaka, Japan

[21] Appl. No.: 916,287

[22] Filed: Aug. 22, 1997

Related U.S. Application Data

[62] Division of Ser. No. 501,053, filed as PCT/JP93/01802, Dec. 13, 1993, published as WO95/16637, Jun. 22, 1995, Pat. No. 5,714,260.

[51] Int. Cl.$^6$ .............................. C09C 1/36; C09D 5/33; C09D 1/00; C01G 49/00
[52] U.S. Cl. ......................... 106/439; 106/436; 424/600; 424/646; 424/59; 428/402
[58] Field of Search .................................... 106/436, 439, 106/459; 424/401, 600, 646, 59; 428/402

[56] References Cited

U.S. PATENT DOCUMENTS

| | | | |
|---|---|---|---|
| 5,165,995 | 11/1992 | Losoi | 428/403 |
| 5,468,289 | 11/1995 | Herget et al. | 106/415 |

FOREIGN PATENT DOCUMENTS

| | | |
|---|---|---|
| 0 192 485 | 8/1986 | European Pat. Off. . |
| 48-67196 | 9/1973 | Japan . |
| 61-264063 | 11/1986 | Japan . |
| 62-67014 | 3/1987 | Japan . |
| 62-83305 | 4/1987 | Japan . |
| 2-178219 | 7/1990 | Japan . |
| 2-204326 | 8/1990 | Japan . |
| 4-5001 | 1/1992 | Japan . |

*Primary Examiner*—Michael Marcheschi
*Attorney, Agent, or Firm*—Cushman, Darby, Cushman, IP Group of Pillsbury, Madison & Sutro LLP

[57] ABSTRACT

Ultrafine iron-containing rutile type titanium dioxide particles useful for UV shielding cosmetics, pharmaceutical compositions and UV shielding paints are disclosed. They are rutile type crystalline titanium dioxide particles having an average single particle size of 0.01 to 0.1 μm and containing an iron component at a concentration of 1 to 15% by weight as expressed as Fe based on the titanium dioxide in the crystalline structure. They can be produced by using a fine titania sol comprising rutile crystallites as basic particles, precipitating iron oxide or hydrated iron oxide onto the surfaces of the titania particles to effect coating, then firing and grinding.

8 Claims, No Drawings

ULTRAFINE IRON-CONTAINING RUTILE TITANIUM OXIDE AND PROCESS FOR PRODUCING THE SAME

This is a division of application Ser. No. 08/501,053, filed as PCT/JP93/01802, Dec. 13, 1993, published as WO95/16637, Jun. 22, 1995, U.S. Pat. No. 5,714,260.

The present invention relates to ultrafine rutile type titanium dioxide particles containing iron, a process for producing the same, and a composition containing the same such as UV shielding cosmetics, pharmaceutical compositions, and UV shielding paints.

BACKGROUND OF THE INVENTION

Prior Art

Ultrafine titanium dioxide particles having a primary particle size of about 0.1 μm or less are transparent to visible lights, i.e., capable of transmitting rays of visible light when incorporated in resin films or shapes, and on the other hand, they can shield ultraviolet rays to protect materials which change a color or denature through exposure to ultraviolet radiation. In this way it has been well known that the ultrafine titanium dioxide particles exhibit different properties than those of pigmentary titanium dioxide particles having a primary particle size of 0.15 to 0.5 μm. For this reason, recently specific attention has been focussed on utilization of the ultrafine titanium dioxide particles as UV shielding cosmetics for preventing sunburn due to UV light. However, the ultrafine titanium dioxide particles which have heretofore been commercially available have so high coagulation force that they are difficult to perfectly disperse at a primary particle level in both water and an oily solvent. For example, when UV shielding cosmetics containing such ultrafine titanium dioxide particles are applied to skin, intensely bluish colored light scatter occurs to impart a bluish tint to the cosmetics, which is a drawback showing the skin unhealthy. Moreover, conventional fine titanium dioxide particles can sufficiently shield ultraviolet rays of wavelengths in the range B (wavelengths in the range from 320 to 290 nm), but are insufficient in shielding ultraviolet rays of wavelengths in the range A (wavelengths in the range from 380 to 320 nm). More recently, there has been a concern about skin disorder owing to ultraviolet rays in the range A and to cope with this problem it is practical to use additionally organic ultraviolet absorbents.

There has been proposed a cosmetic composition comprising fine titanium dioxide particles and fine iron oxide particles which is excellent in UV shielding effect and does not exhibit a bluish tint as, for example, disclosed in JP-A 62-67014. However, a simple mixture of titanium dioxide particles and iron oxide particles may cause a problem of color separation in the cosmetics due to a difference in dispersibility and of insufficient effectiveness in shielding ultraviolet rays in the range A. Recently there have been proposed several methods of forming a unitary pigment comprising titanium dioxide and iron oxide to prevent the aforementioned color separation. For example, there have been proposed (1) a method comprising treating titanium dioxide particles having an average particle size of 0.01 to 1 μm with hydrous iron oxides and then drying and/or firing the treated particles as disclosed in JP-B 4-5001, (2) a method comprising treating titanium dioxide particles having a maximum particle size of 0.1 μm with an iron salt of basic higher fatty acid as disclosed in JP-A 61-264063, and (3) a method comprising treating titanium dioxide particles having a maximum particle size of 0.1 μm or less with an oxide or hydroxide of aluminum, silicon, or iron as disclosed in JP-A 2-204326. However, all these methods employ procedures of using fine titanium dioxide particles, depositing iron hydroxide or oxide on the surfaces of the particles, and drying or firing the treated particles. These methods lead to insufficient reduction in the so-called bluish coloration as well as insufficient shielding effect to ultraviolet radiation in the range A. There has also been proposed a composite titanium dioxide-iron oxide in a ratio of 0.05 to 50 expressed as $Fe_2O_3/TiO_2$ by weight as disclosed in JP-A 2-178219. Although this is for the purpose of improving the titania sol for the insufficient ability of shielding ultraviolet light rays in the range A, it suffers from limitations on the incorporation of the sol into cosmetics, pharmaceutical compositions and paints due to the configuration of sol and still has problems with durability and long term stability.

SUMMARY OF THE INVENTION

The present invention is to provide ultrafine iron-containing rutile type titanium dioxide particles which have a greatly improved ability of shielding ultraviolet radiation in the range A and which are most suitable for UV shielding cosmetics not imparting a bluish tint, pharmaceutical compositions, UV shielding paints and the like.

The present inventors made an intensive research for obtaining ultrafine titanium dioxide particles which are excellent in the ability of shielding ultraviolet radiation in the range A without imparting a bluish tint. As a result, we have found that ultrafine rutile type titanium dioxide particles having an average single particle size of 0.01 to 0.1 μm and an iron component in solid solution in a crystalline structure can be produced by using a fine titania sol comprising rutile crystallites as basic materials and a water soluble salt of iron, neutralizing the water soluble salt of iron in the presence of the sol to precipitate hydrous iron oxides on the surfaces of the titania particles with the surfaces being coated with the precipitates and then firing the coated particles at temperatures of 300° to 850° C.

The thus obtained ultrafine iron-containing rutile type titanium dioxide particles are excellent in the ability of shielding ultraviolet radiation in the range A and the cosmetics containing the titanium dioxide particles incorporated can be applied to skin with a satisfactorily reduced bluish tint. Thus, the ultrafine titanium dioxide particles according to the present invention are characterized by rutile type crystalline titanium dioxide particles having an average single particle size of 0.01 to 0.1 μm and containing an iron component in an amount of 1 to 15% by weight as expressed as Fe based on $TiO_2$ in the crystalline structure.

DETAILED DESCRIPTION OF THE INVENTION

In the present invention a fine titania sol comprising rutile crystallites is used as basic material and the particles in the sol are coated on the surfaces with hydrous iron oxides and then fired to form a solid solution of iron oxide or hydrous iron oxides in the coatings and titanium dioxide in the crystalline structure so that the resultant particles can exhibit quite excellent effects, which could not be achieved in the prior art, in that (1) they do not cause the color separation into the iron component and titanium dioxide even when incorporated in cosmetics, pharmaceutical compositions and paints under strong dispersing conditions, (2) they have markedly increased the ability of shielding ultraviolet radiation in the range A, and that (3) they have less tendency to exhibit a bluish tint. The ultrafine iron-containing rutile type titanium dioxide particles of the present invention have an average particle size of 0.01 to 0.1 μm, preferably 0.02 to 0.08 μm as expressed as an average single particle size determined by electron microphotograph. The amount of the iron component in the solid solution with the crystalline rutile type titanium dioxide is 1 to 15% by weight, preferably 2 to 10% by weight as expressed as Fe based on the titanium dioxide. A higher amount of the iron component than the defined upper limit may cause too strong coloration due to the iron component which is present out of the solid solution in the crystalline structure resulting in problems of impairing the thermal durability and the resistance to chemicals of the titanium dioxide particles. A lower amount of the iron component than the defined lower limit makes it difficult to achieve a satisfactorily reduced bluish tint and satisfactory ability of shielding ultraviolet radiation in the range A.

The ultrafine iron-containing rutile type titanium dioxide particles according to the present invention may contain a small amount of at least one metal element selected from the group consisting of aluminum, zinc, sodium, potassium, magnesium and phosphorus in the crystalline structure together with the aforementioned iron component. This enables controlling of the particle size of the ultrafine iron-containing rutile type titanium dioxide particles to be produced as well as improvement of the durability of the particles. Moreover, the ultrafine rutile type titanium dioxide particles may be coated on the surfaces with at least one selected from the group consisting of oxides and hydroxides of aluminum, silicon, titanium, zirconium, tin and antimony, or at least one selected from the group consisting of organics such as carboxylic acid, polyols, amines and siloxanes. This can further improve the dispersibility of the particles into cosmetics and paints and the durability of the coating films.

A process for producing the ultrafine iron-containing rutile type titanium dioxide particles of the present invention is described under.

In the present invention, specifically a fine titania sol comprising rutile crystallites as basic particles is used and iron oxide or hydroxide is precipitated on the surfaces of the titania particles. The fine titania sol containing rutile crystallites as used here is a sol of fine hydrated titanium dioxide particles which show peaks of rutile crystal as determined by an X-ray diffraction analysis and have generally an average crystallite size of 50 to 120 Å. The fine hydrated titanium dioxide particles are those which can be used as seeds in the step of hydrolysis of titanium sulfate in the production of pigmentary titanium dioxide by a sulfate process for facilitating the formation of rutile type titanium dioxide and controlling the particle size and which are different from ordinary particles of titania hydrates, for example, amorphous metatitanic acid and orthotitanic acid from the standpoints of crystalline structure and surface activity.

These fine titania sols can be made by various methods such as (1) a method comprising hydrolyzing an aqueous solution of titanium tetrachloride at a concentration of 150 to 220 grams $TiO_2$/liter by heating the solution for 2 to 10 hours at the boiling point, (2) a method comprising neutralizing an aqueous solution of titanium sulfate or tetrachloride at a concentration of 150 to 220 grams $TiO_2$/liter with an alkaline solution of sodium hydroxide and the like while keeping the solutions at a temperature of 5° to 30° C. to precipitate colloidal, amorphous titanium hydroxide and aging the resultant colloidal titanium hydroxide at temperatures of 60° to 80° C. for 1 to 10 hours, and (3) a method comprising adding amorphous hydrated titanium oxide such as metatitanic acid or orthotitanic acid into an aqueous solution of sodium hydroxide, heat-treating the mixture at a temperature of 80° C. to the boiling point for 1 to 10 hours, filtrating, washing, and heat-treating the resulting particles in a hydrochloric acid solution at a temperature of 80° C. to the boiling point for 1 to 10 hours.

In the process of the present invention the precipitating the iron oxide and/or hydrated iron oxide onto the surfaces of the titania particles may be accomplished by, for example, adding a water soluble salt of iron to the aforementioned titania sol at a concentration of 1 to 15% by weight, preferably 2 to 10% by weight as expressed as Fe based on the titanium dioxide while heating the titania sol at a temperature of 40° to 90° C., preferably 60° to 80° C., and neutralizing the sol with an addition of an alkaline solution such as caustic soda or ammonia water. The titania sols, to be used may be adjusted to a concentration of titania ($TiO_2$) of 50 to 300 grams/liter, if necessary. The water soluble salt of iron to be added includes ferrous chloride, ferrous sulfate, ferrous nitrate, ferric chloride, ferric sulfate and ferric nitrate. The neutralizing reaction should preferably be conducted while adjusting the system to a pH of 8 to 10.

Next, the product produced in the previous step is separated, washed, then fired after drying or without drying at temperatures of 300° to 850° C., and ground to ultrafine iron-containing rutile titanium dioxide of 0.01 to 0.1 μm. The grinding may be carried out by wet grinding with a sand mill, pebble mill, disk mill or the like, or by dry grinding with a fluid energy mill, hammer mill, or edge runner mill.

In the process of the present invention, the use of the titania sols comprising rutile crystallites as basic particles permits the solid solution of the iron component into the titanium dioxide crystalline structure to easily proceed even when firing at relatively low temperatures and also enables a stable rutile type titanium dioxide ultrafine particles to easily be produced.

In the process of the present invention, onto the surfaces of the ultrafine iron-containing rutile type titanium dioxide particles produced in the process as described above may be precipitated hydrated oxide of metal such as aluminum, silicon, titanium, zirconium, tin or antimony to coat the particles with the hydrated metal oxide. This step can be accomplished, for example, by dispersing the iron-containing rutile type titanium dioxide particles, which are obtained by firing and grinding as above, in water to produce a slurry and, if necessary, wet grinding and classifying the slurry, then adding at least one selected from the group consisting of water soluble salts of at least one metal selected from the group consisting of aluminum, silicon, titanium, zirconium, tin and antimony to the slurry at a concentration of 1 to 30% by weight in total of at least one oxide of at least one metal selected based on the titanium dioxide, and thereafter neutralizing the slurry with an acidic solution of sulfuric acid, hydrochloric acid, or the like when the water soluble salt is alkaline in the slurry, or with an alkaline solution of caustic soda, ammonia water, or the like when the water soluble salt is acidic in the slurry, to cause precipitation on and coating the surfaces of the titanium dioxide particles, separating the coated particles, drying and grinding the resultant particles. This coating treatment can improve the dispersibility in a dispersion medium and the durability of the produced ultrafine iron-containing rutile type titanium dioxide particles.

The ultrafine iron-containing rutile type titanium dioxide particles according to the present invention are useful for a wide variety of UV shielding cosmetics, pharmaceutical compositions and UV shielding paints as described above, and in addition they are suitable for UV shielding paints applicable to wood which have attracted recent interest and are gaining popularity. The ultrafine iron-containing rutile type titanium dioxide particles of the present invention may be incorporated as such in a variety of mediums for applications. Alternatively, they may be incorporated in mediums for applications as aqueous or oily dispersions which are obtained by dispersing the particles in aqueous or oily solvents in the presence of various dispersants. The aqueous or oily dispersions can be prepared by various methods. That is, an aqueous medium comprising primarily water and dispersant(s) such as condensed phosphoric acid compounds, polycarboxylic acid compounds, amino acid compounds, polyoxyethylene alkyl ethers, aminoalcohols and the like when the aqueous dispersions are prepared, or an oily medium such as vegetable oils, animal oils, mineral oils, silicone and the like and dispersant(s) such as polyoxyethylene alkyl ethers, sorbitan fatty acid esters, polyoxyethylene alkylphosphate, fatty acid alkanolamide, polyether-modified silicone oils, silicone resins and the like when the oily dispersions are prepared, are placed with the ultrafine iron-containing rutile type titanium dioxide particles in a grinding machine, for example, a sand mill, pebble mill, disk mill or the like and the mixing and grinding are effected to produce the dispersions. The concentration of solids in the dispersions should be in the range from about 20 to about 70% by weight, preferably about 40 to about 60% by weight.

EXAMPLES

Example 1

To an aqueous solution of titanium tetrachloride at a concentration of 200 grams $TiO_2$/liter while keeping the solution at room temperature was added an aqueous solution of sodium hydroxide and the pH was adjusted to 7.0 to precipitate colloidal amorphous hydrated titanium oxide, followed by aging to produce a rutile type titania sol. This sol was sufficiently washed and then redispersed to produce a slurry containing hydrated titanium oxide particles at a concentration of 200 grams $TiO_2$/liter. This slurry was heated to 70° C. and an aqueous solution of ferrous sulfate at a concentration of 7% by weight as expressed as Fe based on $TiO_2$ (a concentration of Fe of 50 grams/liter) was added to the slurry over 30 minutes under well stirring, and thereafter an aqueous solution of sodium hydroxide was added over 40 minutes to adjust the pH to 9, thereby precipitating hydrated iron oxide on the surfaces of the hydrated titanium oxide particles, thus the particles were coated with the hydrated iron oxide. After further aging for 60 minutes, filtration and washing were conducted. The resulting washed cake was fired at 600° C. for 3 hours, redispersed in water, and wet ground with a sand mill to produce a slurry of ultrafine titanium dioxide particles.

This slurry was heated at 70° C. and an aqueous solution of aluminum sulfate at a concentration of 2.0% by weight as expressed as $Al_2O_3$ based on $TiO_2$ was added to the slurry over 30 minutes under well stirring, and then a solution of sodium hydroxide to adjust the pH to 7.0, thereby precipitating hydrated alumina to coat the particles therewith.

After further aging for 60 minutes, filtration, washing and drying were conducted. Then the resulting cake was ground by means of a fluid energy mill to yield ultrafine titanium dioxide particles having an average single particle size of 0.04 $\mu$m as determined by electron microphotograph (A).

Example 2

50 parts by weight of the ultrafine iron-containing rutile titanium dioxide particles obtained in Example 1 were added to 49 parts by weight of refined water, and one part by weight of sodium hexametaphosphate was added to the mixture, and after mixing, the whole was ground with mixing with a sand mill with zirconia beads as grinding medium to yield an aqueous dispersion (B) (viscosity: 95 cP, pH:: 8.2).

Comparative Example 1

The same procedure as in Example 1 was repeated, except that the aqueous solution of ferrous sulfate was not added, to produce ultrafine titanium dioxide particles (C).

Comparative Example 2

The same procedure as in Comparative Example 1 was repeated, except that an aqueous solution of ferrous sulfate at a concentration of 7% Fe by weight was added instead of adding the aqueous solution of aluminum sulfate at a concentration of 2.0% $Al_2O_3$ by weight over 30 minutes, to produce ultrafine titanium dioxide particles (D).

Comparative Example 3

The ultrafine titanium dioxide particles (D) from Comparative Example 2 were fired at 600° C. for 3 hours and ground with a fluid energy mill to produce ultrafine titanium dioxide particles (E).

Comparative Example 4

A commercially available ultrafine iron oxide particles (a particle size of 0.04 $\mu$m) were added to the ultrafine titanium dioxide particles (C) from Comparative Example 1 at a concentration of 7% by weight as expressed as Fe based on the titanium dioxide and mixed to yield a powdery mixture (F).

Comparative Example 5

A commercially available pigmentary iron oxide particles (a particle size of 0.2 $\mu$m) were added to the ultrafine titanium dioxide particles (C) from Comparative Example 1 at a concentration of 7% by weight as expressed as Fe based on the titanium dioxide and mixed to yield a powdery mixture (G).

Test Procedure

The ultrafine titanium dioxide particles (A) and (C) to (G) were incorporated into a sunscreen cream according to the preparation as described below. Moreover, the aqueous dispersion of the sample (B) was incorporated at a concentration of 3.0 parts by weight based on the weight of the titanium dioxide into a sunscreen cream also according to the following preparation (with 51.1 parts by weight of refined water):

|  |  |
|---|---|
| (1) Stearic acid | 2.5 parts by weight |
| (2) Bleached beeswax | 3.5 parts by weight |
| (3) Cetanol | 3.5 parts by weight |
| (4) Squalane | 17.0 parts by weight |
| (5) glycerin monostearate | 3.0 parts by weight |
| (6) Ultrafine titanium dioxide particles | 3.0 parts by weight |
| (7) Methylparaben | 0.1 parts by weight |
| (8) Glycerin | 12.0 parts by weight |
| (9) Triethanolamine | 1.0 parts by weight |
| (10) Refined water | 54.1 parts by weight |
| (11) Perfume | 0.3 parts by weight |

Components (1) to (6) were mixed under heat at 80° C. and added to a mixture which had been obtained by mixing components (7) to (10) under heat at 80° C., and the whole was intimately mixed in a homomixer under powerfully stirring. The component (11) was added at about 45° C. to produce the sunscreen cream.

Evaluation Procedure 1

Each cream was applied onto a quartz glass sheet to a thickness of 25 $\mu$m and evaluated for transmittance by means of a spectrophotometer in the range from 750 to 300 nm.

Evaluation Procedure 2

Each cream was ordinarily used by 10 women of an age from 20 to 52 to make evaluation for an feel to spreadability of the cream on the skin and also visual evaluation on bluish tint with mutually discussing.

The results of the evaluations are shown in Table 1:

TABLE 1

|  | Sample | Transmittance (%) | | | Bluish Tint Imparted to Cream | Feel in Use of Cream |
|---|---|---|---|---|---|---|
|  |  | Visible Light Range (550 nm) | UV Range A (375 nm) | UV Range B (300 nm) |  |  |
| Example 1 | A | 74.3 | 35.3 | 23.5 | 1 | 6 |
| Example 2 | B | 75.6 | 18.8 | 15.1 | 1 | 10 |
| Comp. Ex. 1 | C | 77.3 | 41.3 | 27.3 | 8 | 5 |
| Comp. Ex. 2 | D | 74.3 | 42.7 | 29.9 | 4 | 3 |
| Comp. Ex. 3 | E | 75.9 | 46.0 | 33.0 | 4 | 6 |
| Comp. Ex. 4 | F | 75.4 | 40.9 | 26.8 | 6 | 5 |
| Comp. Ex. 5 | G | 74.3 | 44.6 | 30.0 | 8 | 7 |

Note:
Feel in Use of Cream and Bluish Tint Imparted to Cream were evaluated on a 10 rating scale. The larger the number, the higher the extendability of the cream and the deeper the bluish tint.

The ultrafine iron-containing rutile type titanium dioxide particles produced by the present invention contain an iron component in the solid solution with the titanium dioxide in the crystalline structure thereof so that they have remarkably excellent effects in that (1) they do not cause color separation into the iron component and the titanium dioxide even when incorporated in cosmetics, pharmaceutical compositions and paints under powerfully dispersing conditions, (2) they have markedly increased ability of shielding ultraviolet radiation in the range A when they are incorporated in UV shielding cosmetics and pharmaceutical compositions, and that (3) the cosmetics and pharmaceutical compositions into which the present titanium dioxide particles are incorporated can be applied onto skin to show the skin healthy without causing intensively bluish scattering. Moreover, when the present titanium dioxide particles are incorporated in UV shielding paints for wood, they have excellent UV shielding effects and can impart preferred tint. Furthermore, the aqueous or oily dispersions of the aforementioned ultrafine iron-containing particles enable simplification of mixing and grinding steps in the course of the incorporation into a variety of systems for applications without causing any generation of dust. In addition there can easily be obtained compositions having a high dispersibility with an enhanced UV shielding effect, which compositions allow the cosmetics and pharmaceutical compositions to have more improved stability and much better feel in use.

We claim:

1. An oily dispersion comprising ultrafine iron-containing rutile titanium dioxide particles, wherein said rutile titanium dioxide particles have a crystalline structure, an average particle size of 0.01 to 0.1 μm and contain an iron component in solid solution at a concentration of 1–15% by weight as expressed as Fe based on the titanium dioxide in the crystalline structure.

2. A UV shielding cosmetic or pharmaceutical composition comprising ultrafine iron-containing rutile titanium dioxide particles, wherein said rutile titanium dioxide particles have a crystalline structure, an average particle size of 0.01 to 0.1 μm and contain an iron component in solid solution at a concentration of 1–15% by weight as expressed as Fe based on the titanium dioxide in the crystalline structure.

3. A UV shielding paint comprising ultrafine iron-containing rutile titanium dioxide particles, wherein said rutile titanium dioxide particles have a crystalline structure, an average particle size of 0.01 to 0.1 μm and contain an iron component in solid solution at a concentration of 1–15% by weight as expressed as Fe based on the titanium dioxide in the crystalline structure.

4. An aqueous dispersion containing ultra fine iron comprising rutile titanium dioxide particles, wherein said rutile titanium dioxide particles have a crystalline structure, an average single particle size of 0.01 to 0.1 μm and contain an iron component in solid solution at a concentration of 1 to 15% by weight as expressed as Fe based on the titanium dioxide in the crystalline structure.

5. A UV shielding cosmetic or a pharmaceutical composition comprising the aqueous dispersion of claim 4.

6. A UV shielding cosmetic or a pharmaceutical composition comprising the oily dispersion of claim 1.

7. A UV shielding paint comprising the aqueous dispersion of claim 4.

8. A UV shielding paint comprising the oily dispersion of claim 1.

* * * * *